United States Patent
Wilhelm

(10) Patent No.: US 6,357,281 B1
(45) Date of Patent: Mar. 19, 2002

(54) METHODS AND APPARATUS FOR DETECTING RHEOLOGICAL PROPERTIES OF A MATERIAL

(75) Inventor: Manfred Wilhelm, Maikammer (DE)

(73) Assignee: Max-Planck Gesellschaft zur Forderung der Wissenschaften e.V. (DE)

( * ) Notice: Subject to any disclaimer, the term of this patent is extended or adjusted under 35 U.S.C. 154(b) by 0 days.

(21) Appl. No.: 09/463,489

(22) PCT Filed: Jul. 31, 1998

(86) PCT No.: PCT/EP98/04817

§ 371 Date: Mar. 13, 2000

§ 102(e) Date: Mar. 13, 2000

(87) PCT Pub. No.: WO99/06816

PCT Pub. Date: Feb. 11, 1999

(30) Foreign Application Priority Data

Jul. 31, 1997 (DE) .......................................... 197 33 114

(51) Int. Cl.[7] ............................................. G01N 11/00
(52) U.S. Cl. .................... 73/54.24; 73/54.37; 73/54.41; 73/54.25
(58) Field of Search ............................. 73/54.24, 54.25, 73/54.01, 54.14, 54.31, 54.37, 54.39, 54.41

(56) References Cited

U.S. PATENT DOCUMENTS

| | | | | |
|---|---|---|---|---|
| 2,518,348 A | * | 8/1950 | Mason | 73/54 |
| 3,131,515 A | * | 5/1964 | Mason | 51/58 |
| 3,194,064 A | * | 7/1965 | Miles | 73/101 |
| 3,903,732 A | * | 9/1975 | Rork et al. | 73/54 |
| 4,117,716 A | * | 10/1978 | Simon | 73/32 A |
| 4,602,501 A | * | 7/1986 | Hirata | 73/54 |
| 4,646,754 A | * | 3/1987 | Seale | 128/774 |
| 4,763,512 A | * | 8/1988 | Taylor | 73/54 |
| 4,920,787 A | * | 5/1990 | Dual et al. | 73/54 |
| 5,094,100 A | * | 3/1992 | Dealy et al. | 73/54 |
| 5,113,353 A | * | 5/1992 | George | 364/508 |
| 5,533,381 A | * | 7/1996 | Seale | 73/19.03 |
| 5,750,884 A | * | 5/1998 | Field | 73/54.24 |

OTHER PUBLICATIONS

Nhan Phan–Thien et al. *Micro–Fourier rheometer: Inertial effects*, Rheol Acta 35: 410–416 (1996)© Steinkopff Verlag 1996.

* cited by examiner

*Primary Examiner*—Hezron Williams
*Assistant Examiner*—David J. Wiggins
(74) *Attorney, Agent, or Firm*—Schnader Harrison Segal & Lewis LLP

(57) ABSTRACT

To detect rheological material properties of a fluid, flowable or elastic material, the material is exposed to harmonic excitation with at least one fundamental and at least one parameter F is measured that is variable in response to the harmonic excitation and suitable for determining a new material parameter, whereby measurement of the parameter F comprises recording of a time function F(t) of the parameter and the time function F(t) is subjected to Fourier transformation to form a shear spectrum in which the rheological material properties can be detected from the position of the frequency components, their intensity and/or their dependence on the fundamental.

16 Claims, 2 Drawing Sheets

METHODS AND APPARATUS FOR DETECTING RHEOLOGICAL PROPERTIES OF A MATERIAL

FIELD OF THE INVENTION

The invention relates to methods for detecting rheological material properties, especially for measuring rheological parameters, eg viscosity, of fluid, flowable or elastic materials and for classifying the dynamic response of the materials on the basis of the measured parameters, and apparatus for implementing the methods.

BACKGROUND

In the motion of fluid or flowable materials (generally referred to in what follows as fluids), microscopic interactions of the fluid particles occur that affect the macroscopic response (viscosity) as internal resistance or internal friction and, for example, influence the mobility, fluidity, manipulability, etc of the fluid.

The macroscopic response of a moved fluid is quantified in particular by viscosity $\eta$, which, according to equation (1), is in a relation to the force F that must be produced in order to move two parallel plates (liquid layers) of area A and interplate distance d contrary to one another with the shear velocity v:

$$F/A = \eta \cdot v/d$$

or $$F \sim \eta v = \eta \dot{x} \quad (1)$$

At a sufficiently low shear rate v/d, $\eta$ is a material constant. In this case one speaks of Newtonian viscosity or Newtonian fluids. It is known that, when a certain shear rate is exceeded, the force F no longer increases proportionally to the shear velocity v. In this case of so called non-Newtonian viscosity or non-Newtonian fluids there is thickening or thinning of shear accompanied by an increase or decrease of the necessary shear forces respectively and increase of velocity.

Description of the transition from the linear case of Newtonian viscosity to the nonlinear case of non-Newtonian viscosity and characterization of the nonlinear state are of great technical significance because thickening or thinning of shear at all shear rates relevant in practice occurs in technical operations like pumping, injection molding, extruding or stirring or in hydraulic systems like viscose couplings.

It is generally known that viscosity can be detected by different measuring arrangements, like a capillary viscosimeter, falling body viscosimeter, oscillating disk viscosimeter, etc. But measurement of the nonlinear state was very elaborate to date, or only possible with restrictions. Recording of viscosity as a function of velocity is either not possible with the known arrangements, or it is very time-consuming and offers a low measure of accuracy. Nor are there any practically usable realtime viscosity measurements for technical processes.

Another problem in handling flowing fluids is detection of position/time functions in order to determine velocity or acceleration. In principle this is possible, but the results in practical applications are of no use because the measured raw data are extremely sensitive to noise. The problems mentioned for the known methods of measurement not only affect viscosity but also related material parameters like relaxation times in a nonlinear state or energy dissipation through internal friction.

The publication by D. R. Gamota et al. in "J. Rheol.", vol. 37, 1993, p 919 ff, tells us of analysis of the viscoelastic response only of electrorheological materials using Fourier analysis of shear response signals after harmonic excitation of the material. The viscoelastic response is described as a function of the amplitude of an external high voltage.

In the publication of J. M. Reimers et al. in "Journal of Rheologie", Vol. 40, 1996, p 167, rheological investigations of concentrated polystyrene solutions are described. For an evaluation of the non-linear response, measuring signals are subjected to a Fast Fourier Analysis in order to obtain a qualitative delimitation of linear and non-linear responses of the investigated material. I. M. Krieger et al. describe in "Rheol. Acta", Vol. 12, 1973, p 567, a rheometer for oscillation investigations with non-linear liquids, wherein a Fast Fourier Analysis is conducted for evaluating the measuring variables. U.S. Pat. No. 4,754,640 discloses a rheometer for determining the linear viscoelastic properties of liquids.

SUMMARY OF THE INVENTION

The object of the invention is to provide improved methods for detecting rheological material properties, eg viscosity, of fluid or flowable materials, allowing in particular fast and precise measurement in the linear and/or non-linear state of the investigated material. The invention also intends to provide an apparatus for implementing the methods.

The invention is based on the idea of departing evaluation of a measured signal that characterizes the material's response to the excitation in a conventional method of measuring viscosity (eg with an oscillating disk viscosimeter) after harmonic excitation of the material to be investigated, and instead of evaluating the measured signal by detecting its function of time and Fourier transformation in the frequency domain. The inventors have determined for the first time that, in a conventional viscosity measurement really intended only for materials in a linear or Newtonian state, further information about rheological material properties, especially in a nonlinear or non-Newtonian state, become available upon transition to the frequency domain.

Rheological material properties are all properties that characterize the internal friction and thus the flow behavior of the investigated material and their dependence on shear velocity, temperature, pressure and the like. Harmonic excitation is any form of excitation of mechanical oscillations of the mass elements of an investigated material according to a harmonic time function. This is preferably presented as a sinusoidal function, but may also be superimposition of a large number of sinusoidal functions. Harmonic excitation is preferably produced by a mechanical oscillating device that is part of a conventional oscillating disk viscosimeter for example. The measured signal characterizing the material response to the excitation is, in the case of an oscillating disk viscosimeter for example, a force (or torque) produced in the material by the mechanical oscillating device or otherwise a compressive force transmitted by the material.

The measured force variable can be a macroscopic force or a measured variable that is characteristic of the local stress or locally acting force in the material. A local force, variable, for example, can be determined on the basis of the stress optical relation by an optical measurement. As an example, it is possible to determine the intensity of the optical double refraction in the material as a function of time during mechanical excitation of the material. According to the stress optical relation, the optical double refraction is in a linear relation to the local force, so, according to the invention, evaluation of the time function of the intensity of the optical double refraction may be analogous to the evaluation of macroscopic force variables.

According to the invention, the Fourier transformation of the time function of the measured signal generates a shear spectrum, from which the parameters of a Taylor series expansion of the viscosity, linear or nonlinear response of the material, a state of shear thickening or shear thinning, nonlinear relaxation times in the material (after reverse Fourier transformation of position/time functions), velocities and/or accelerations of the mass elements of flowing fluids and/or so-called memory effects in the material can be extracted.

An apparatus according to the invention contains a device (eg oscillating disk or rotational viscosimeter) for measuring the time function of a characteristic rheological parameter, a device for Fourier transformation of the time function and/or reverse transformation, and a control and display unit for setting the operating parameters of the measuring device and data transfer from the transformation device. The measuring device can be part of a control circuit for detecting the start of transition of the material to nonlinear response or shear thickening or shear thinning.

If an optical measurement (intensity of double refraction) is made, the measuring device is modified accordingly by providing transparent excitation elements. For example, the limiting plates on the material to be investigated, by which exciting forces are to be transmitted to the material, can be produced of glass. An optical measurement presents hardware has advantages as regards measuring the time function of the forces acting in the material.

The Fourier analysis provided by the invention allows determination of the nonlinear terms of the viscosity in relation to the velocity or the frequency from the intensities of the higher harmonics of the Fourier spectra. Criteria are also given for nonlinear response of the examined fluids.

The invention is of special advantage in rheological investigations on materials with high nonlinearity even at the smallest shear rates. There are polymers, for example, that exhibit nonlinear behavior under shear. The relaxation times of the molecules in the polymer are so large that they can no longer be detected with technically feasible, low shear rates. The material goes straight into a nonlinear state (eg shear thinning). To enable determination of the shear rate at which the nonlinear response begins in these materials too, the invention foresees measuring the intensity of the overtones (components of higher frequency in the Fourier transformed shear spectrum) for different frequencies and amplitudes. It was found, for example, that the intensity of the overtone corresponding to three times the fundamental increases exponentially with the amplitude of material excitation. Therefore, when recording the dependence of the overtone intensity on the amplitude of the excitation, it is possible to deduce conditions (shear rate, amplitude) where of the third overtone. The shear rate of the onset point is determined by reverse extrapolation from the frequency and amplitude functions of the overtones is below a specified value. For the first time the invention allows determination of the transition region between so-called linear and nonlinear response in the case of samples where observation of linear response with technically feasible shear rates is difficult or not possible at all.

Methods and apparatus according to the invention possess the following advantages:

Complete characterization of nonlinear response (eg shear thickening or thinning) in the Fourier domain is possible for the first time, whereby both the amplitudes and the phases of higher harmonic components are detected. Relaxation times in states of non-equilibrium can be characterized. The shear data can be reconstructed basically free of noise and thus the velocity or acceleration response of the examined material can be analyzed. With a shear cycle it is possible to detect any number of shear rates (ie multiplex benefit), because a large number of shear velocities are always contained in a harmonic excitation. The measuring speed is high, allowing realtime viscosity measurement in nonlinear state. Memory effects can be measured, recognizable in the Fourier spectrum as intensity at even-numbered multiples of the excitation frequency.

The materials investigated by the invention comprise all fluid or flowable materials, especially fluid solutions, dispersing agents, emulsions, melts or flowable plastics. The materials investigated by the invention may also be gaseous or vaporous materials or elastic solids (eg rubber-like materials).

BRIEF DESCRIPTION OF THE DRAWING

Embodiments and further advantages of the invention are described with reference to the attached drawings, which show.

DETAILED DESCRIPTION OF THE INVENTION

Figure 1:
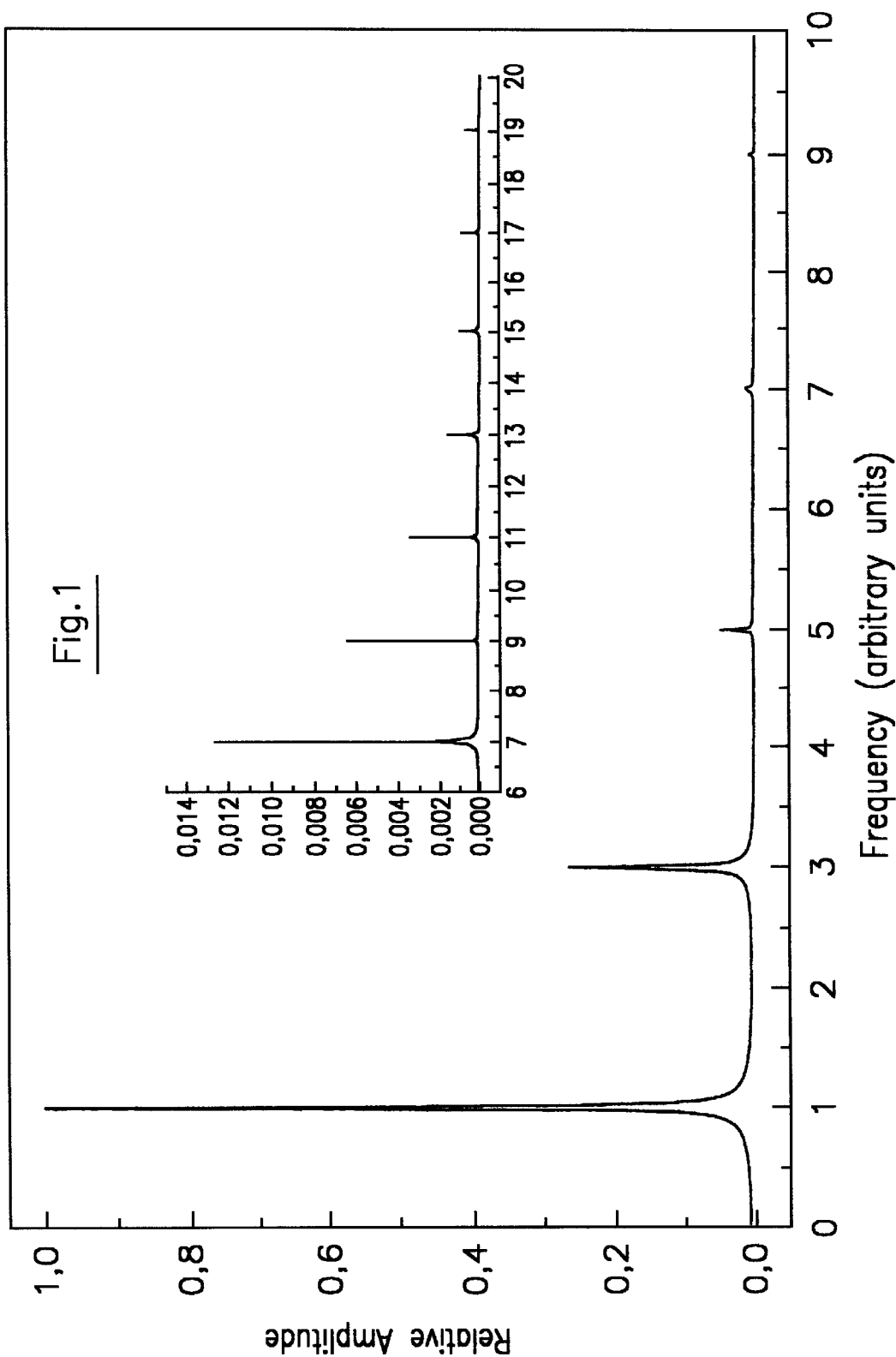
FIG. 1 Curve to illustrate a Fourier amplitude spectrum.

The following explanation exemplifies detection of viscosity by measurement of shear force with a rotational viscosimeter. But the invention is not restricted to this, it can be used for all arrangements that provide for harmonic excitation of an investigated material and recording of a signal that is characteristic of motion of the fluid in response to the excitation. Furthermore, the invention is not restricted to measurement of viscosity but can be used for related material parameters like relaxation times in a nonlinear state or energy dissipation through internal friction.

To begin with, the mathematical fundamentals for the method according to the invention are described. The classic rheological description of the motion of a mass element (position-time-function) is given by differential equation (2): for the forces $$m\ddot{x} + \eta\dot{x} + kx = A_0 \exp(i\omega t) \qquad (2)$$

resolved as:

$$x = B_0 \exp(i\omega t + \delta) \qquad (3)$$

Harmonic excitation of a fluid with the frequency $\omega$ (right half of equation (2)) consequently produces a harmonic response function of the same frequency $\omega$, but with a characteristic phase shift $\delta$, that describes the relationship of stored (k) to dissipated ($\eta$) energy.

In the non-Newtonian case we find $\eta = \eta(v)$ with the symmetry relation $\eta(v) = \eta(-v) = \eta(|v|)$. This basis on the idea that a reversal of velocity also means a reversal of force, i.e.—viscosity to a first approximation is only dependent on the magnitude of the velocity. Viscosity may be developed as a function of velocity in a Taylor series expansion. The development can refer to the frequency of the excitation or the velocity. The invention is not restricted to the velocity-related Taylor series expansion named here. As an alternative, a time-related Taylor series expansion can be used or, depending on application, any other analytical form of presenting viscosity. If, for example and depending on material, viscosity is proportional to the reciprocal value of the velocity, the following considerations can be made analogous to the particular analytical form of such proportionality. In what follows a Taylor series expansion is considered around v=0 (the factors $\eta_0$, a, b, c . . . n can be complex numbers):

$$\eta=\eta_0+a\,|v|+b\,|v|^2+ \quad (4)$$

After harmonic excitation according to $$x=A_0\exp(i\omega_1 t) \quad (5)$$

or $$v==i\omega_1 A_0\exp(i\omega_1 t) \quad (5)$$

the absolute value of the velocity by Fourier analysis can be presented according to equation (6):

$$|v|=||=|i\omega_1 A_0\exp(i\omega_1 t)|$$

$$|v|\sim 2/\pi - 4/\pi\left(\frac{\cos 2\omega_1 t}{3}+\frac{\cos 4\omega_1 t}{15}+\frac{\cos 6\omega_1 t}{35}\ldots\right)$$

$$|v|\sim a'+b'\cos(2\omega_1 t)+c'\cos(4\omega_1 t)+ \quad (6)$$

Accordingly higher harmonics of the fundamental frequency $\omega_1$ are generated by excitation. Because of the dependence on the absolute value of the shear velocity v, equation (6) only contains even-numbered harmonics of the fundamental frequency $\omega_1$. From equations (1), (4) and (6) we obtain:

$$F\sim i\omega_1 A_0(\eta_0+a|v|+b|v|^2+\ldots)\exp(i\omega_1 t)$$

$$F\sim (\eta_0+a|v|+b|v|^2+\ldots)\exp(i\omega_1 t)$$

$$F\sim \{\eta_0+a[a'+b'\cos(2\omega_1 t)+c'\cos(4\omega_1 t)+\ldots]+$$

$$b[a'+b'\cos(2\omega_1 t)+c'\cos(4\omega_1 t)+\ldots]^2\ldots\}\exp(i\omega_1 t) \quad (7)$$

After conversion and complex notation of the cos function, equation (7) produces:

$$F\sim a''\exp(i\omega_1 t)+b''\exp(i3\omega_1 t)+c''\exp(i5\omega_1 t)+ \quad (8)$$

The shear force F is an example of a parameter that, according to the invention, is measured and detected as a function of time by a viscosimeter after harmonic excitation with maximum amplitude $A_0$. Other examples, like in particular optical double refraction as a measurement parameter, are cited above.

To determine rheological properties of the investigated material, the time function F(t) is subjected to Fourier analysis, whereby the amplitude and/or phase spectrum of the Fourier transformation is determined and/or the following data conversions are considered. Details of sampling the time function and determining the Fourier transformation are not given here because this follows the familiar algorithms, as described for example in "FFT-Anwendungen" by E. O. Brigham (Oldenbourg, Munich 1997) incorporated herein by reference with regard to the generation of continuous Fourier Spectra.

(a) Determining parameters $\eta_0$, a, b, etc

The amplitude Fourier analysis (equation (8)) of the time function F(t) produces what is called a shear spectrum with intensities at $\omega_1$, $3\omega_1$, $5\omega_1$, etc. According to equations (7) and (8), the intensity at these points relates to the linear and nonlinear parameters $\eta_0$, a, b, etc of the viscosity according to the development (4).

Further evaluation therefore comprises calculation of the absolute values $\eta_0$, a, b, etc as a function of velocity v from the amplitude $A_0$ and the fundamental frequency $\omega_1$ from equations (4) through (8).

(b) Determining transition between Newtonian and non-Newtonian state

Only the first two terms of the Taylor series expansion according to equation (4) are considered for characterizing the transition between a Newtonian and a non-Newtonian state. The differential equation (2) is then:

$$A_0\exp(i\omega t)=m\ddot{x}+\eta_0\cdot\dot{x}+kx+a|\dot{x}|\dot{x} \quad (9)$$

with a linear proportion that would have the above solution (3) and a nonlinear proportion $(a|\dot{x}|\dot{x})$ that causes a deviation from the solution (3). The extent of the perturbation, especially upon transition from a Newtonian to a non-Newtonian state, therefore depends decisively on the nonlinearity parameter a, which corresponds to the second term in the Taylor series expansion (4).

Therefore, to characterize the response of a fluid according to the invention, the parameter "a" versus shear velocity or shear rate is determined, for example, by variation of the excitation or fundamental frequency and possibly compared to predetermined limits.

FIG. 1 shows the curve of a simulated spectrum with shear thinning, in which reduction of viscosity to 30% of the Newtonian value is assumed (assumption of viscosity and development parameters as real, non-complex quantities). It can be seen that the spectrum, even on breakoff of the Taylor series expansion (4) after the linear term, contains higher harmonics (figure inside on different scale). This is an especially advantageous result of the symmetry relation of the velocity function used in the invention. The time function of the magnitude of a sinusoidal velocity pattern has peak regions at the minima that contribute decisively to forming higher components in the shear spectrum.

(c) Determining nonlinear response

The following considerations serve for characterizing the limit case of the non-Newtonian state with extreme shear thinning. Extreme shear thinning means that, according to (10), the viscosity disappears above a critical velocity $v_c$:

$$\eta=\eta_0 \text{ for } v<v_c \text{ or } \eta=0 \text{ for } v\geq v_c \quad (10)$$

The shear force can then be stated as a step function whose Fourier development is according to (11):

$$F\sim [\exp(i\omega_1 t)+\tfrac{1}{3}\exp(i3\omega_1 t)+] \quad (11)$$

The invention defines a criterion for the degree of non-Newtonian response based on the intensity relationships in a Fourier spectrum of the shear force and, by comparison of a measured result with the demarcation criterion, allocates the investigated fluid to one of the responses.

A demarcation criterion is produced, for example, from the amplitude ratio (or ratio of intensities I) of the lowest two frequencies $I(3\omega_1)/I(\omega_1)=\frac{1}{3}$ or from the envelope of the development coefficients according to $I(\omega)\sim 1/\omega$ or from the amplitude ratios at more than the two lowest frequencies.

Alternatively, nonlinear response can be detected by comparison of measured results with simulation data data, such as when the intensity ratio is smaller than or substantially equals a constant. A peak height distribution is determined from the intensity relationships in the Fourier spectrum of the shear force and compared to simulation data of a model or reference material. The simulation data comprise a peak height distribution recorded for certain simulation parameters or certain measurement parameters. Selection of the frequency and/or phase components of the Fourier spectrum considered for determining the peak height distribution is a matter of application.

(d) Determining shear thickening

The intensity ratio $V=I(3\omega)/I(\omega)$ as a function of the fundamental $\omega$ behaves as follows. At low shear gradients (linear response) the ratio is approximately zero. At very high shear gradients where the coupling between the surfaces is very strong, the shear force according to the equations (2) and (3) is simply given by the constant term. The function $V(\omega)$ reaches a maximum in the amplitude shear spectrum according to equation (9) where interference and nonlinearity are maximum. Nonlinear response can be detected before the maximum is reached however, eg when $I(3\omega_1) > 0$ applies for the intensity of the first overtone. As soon as the overtone corresponding to $3_{107\ 1}$ appears in the spectrum, the nonlinear response of the investigated material is detected.

According to the invention therefore, the function $V(\omega)$ is recorded to characterize the rheological response of a fluid. From $V_{max}$ it is possible to determine the degree of shear thickening or thinning. For further characterization of the rheological response, the function $V(\omega)$ is recorded for different amplitudes of the harmonic excitation of the investigated material.

(e) Detecting relaxation processes

At a molecular level the transition from linear to nonlinear response is to be understood in that a molecule (eg polymer) exercising a shear force with sufficiently high shear rate or shear velocity no longer has time to adopt its (basic) conformation of the unloaded state, so that interaction with the neighboring molecules no longer changes linearly with the shear rate. The molecule form is then itself a function of velocity. The mean time to adopt basic conformation in linear response is called the linear relaxation time $\tau$. In the case of polymers, for instance, it is very much dependent on mass ($\tau \sim M^2$ or even $\tau \sim M^3$)

According to the invention, detection of the nonlinear state means that the nonlinear relaxation times are detected as a function of the shear rate (or fundamental) in different states of non-equilibrium.

(f) Reverse Fourier transformation

To determine the velocity or acceleration of the mass elements of flowing fluids from position-time-functions, the invention makes use of the fact that a Fourier transformation is reversible.

The discrete Fourier spectrum of the digitally detected time function $S(t)$ of the measured parameter S is transformed back to form complex time data from which both the amplitude and the phase of all harmonics can be determined. Thus the original time signal is entirely reconstructed according to:

$$S(t) = \sum_n A_n \cos(n\omega_1 t + \phi_n) \quad (12)$$

From $S(t)$ it is possible to determine the velocity and/or acceleration for every point during a shear cycle with high accuracy and speed, so in practical applications the velocity and/or acceleration of a substance in a technical system can be predicted.

(g) Detecting memory effects in investigated material

All shear gradients appear twice during a full shear cycle. The above deductions were made assuming independence of viscosity from the sense of velocity and led to the contribution of odd multiples of the fundamental in the Fourier spectrum. If even multiples of the fundamental now also appear in the Fourier spectrum, this means viscosity is a function of direction.

According to the invention, the Fourier spectrum is thus checked for even-numbered multiples of the fundamental. The appearance of even multiples and their intensity allow a statement about memory effects (e.g. slip) that characterize viscosity as a function of whether the shear stress is being built up or released.

The procedures (a) through (g) described above can be performed by the invention as a function of temperature. According to FIG. 2, an apparatus as invented includes a device 10 for measuring the time function of a characteristic rheological parameter, a device 20 for Fourier transformation of the time function into the Fourier domain and reverse transformation, and a control and display unit 30 for setting the operating parameters of the measuring device 10 and transfer of data from the transformation device 20. The measuring device 10, for example, is a temperature-stabilized oscillating disk or rotational viscosimeter or another measuring instrument that is designed for applying harmonic excitation to a fluid for examination and detecting a response signal. The control and display unit 30 and the transformation device 20 can be set up as one unit, eg in a personal computer.

The invention is suitable for all technical processes in which the rheological properties of a fluid are of interest. It is possible to characterize flow mechanisms in non-equilibrium states, eg extruding, injection molding, stirring, pumping, laminar casting of polymers, solutions, emulsions and the like.

Figure 2:
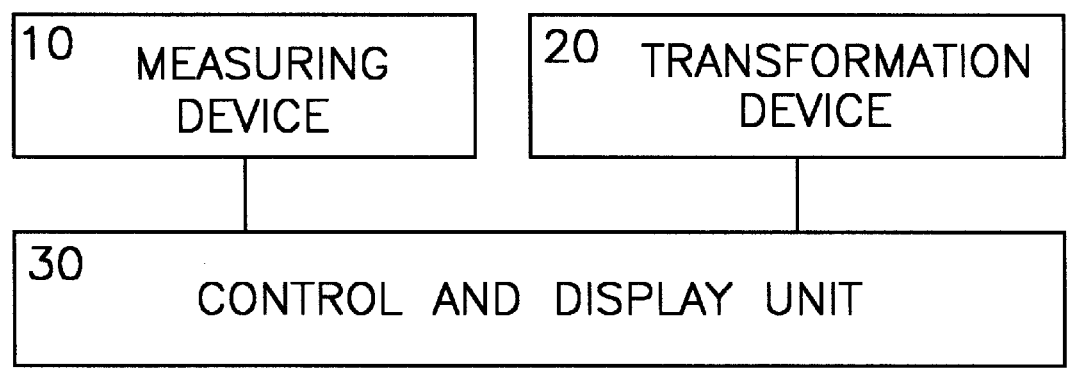
FIG. 2 Schematic of an embodiment of the apparatus according to the invention.

Since the invention is a sensitive means of detecting the transition from linear to nonlinear response of a flowing fluid, the invention also covers monitoring systems for implementing the methods according to the invention. To avoid unnecessary losses of energy when transporting a fluid, an apparatus according to FIG. 2 can be connected to a system in which fluids are moved. As soon as the control and display unit detects the beginning of transition to nonlinear response or to shear thickening, a signal is issued to a drive and/or temperature stabilizing system so that movement of the fluid is influenced accordingly. The apparatus according to FIG. 2 is in this case part of a control loop.

What is claimed is:

1. A method for detecting rheological material properties comprising:

harmonically exciting the material with at least one fundamental frequency $\omega_1$, measuring at least one parameter F that is variable in response to the harmonic excitation and is suitable for determining material properties of the material, by recording a time function F(t) of the parameter F, wherein said material properties are parameters of a Taylor series expansion or an analytical presentation of said material property depending on velocity or time, transforming by Fourier transformation the time function F(t) to form a shear spectrum in which said rheological material properties can be detected from the location of the frequency components, the intensity and/or function of the fundamental frequency $\omega_1$, and determining a shear velocity or shear rate function or the ratios of the intensities of the frequency components of the shear spectrum and comparing the result to predetermined limits or a demarcation or simulation criterion to detect a linear or nonlinear response.

2. A method according to claim 1 in which the rheological material properties are parameters $\eta_0$, a, b, c, . . . n of a Taylor series expansion of viscosity $\eta$ according to $\eta=\eta_0+a|v|+b|v|^2+\ldots \eta$.

3. A method according to claim 1 or 2 in which the demarcation criterion is the ratio of intensity I of the two lowest frequency components $I(3\omega_1)/I(\omega_1)$ and a nonlinear response is detected when the intensity ratio is smaller than or substantially equals a constant.

4. A method according to claim 1 or 2 in which the demarcation criterion is an envelope of the intensities of the shear spectrum, and a nonlinear response is detected when the intensities behave according to $I(\omega) \sim 1/\omega$.

5. A method according to claim 1 or 2 in which a nonlinear response is detected when $I(3\omega_1)>0$ applies for the intensity I of the frequency component $3\omega_1$.

6. A method according to claim 1 in which the frequency $\omega$ of the harmonic excitation varies and the dependence $V(\omega)$ of the intensity ratio $V=I(3\omega)/I(\omega)$ on the fundamental $\omega_1$ is determined, whereby a state of maximum nonlinearity is detected when the intensity ratio $V(\omega)$ is at a maximum.

7. A method according to claim 6 in which the amplitude of the harmonic excitation is varied and the dependence of the nonlinear rheological response on the amplitude is detected.

8. A method according to claim 1 in which the response as characterized by nonlinear relaxation times in the material are detected as a function of shear rate or fundamental $w_1$ in a set of different possible states of non-equilibrium for said material.

9. A method according to claim 2 in which it is determined whether even multiples of the fundamental $w_1$ appear in the shear spectrum to detect the sense dependence of viscosity on buildup or release of shear stress.

10. A method according to claim 1 in which, to determine position-time-functions, velocities and/or accelerations of mass elements of flowing fluids, the Fourier transformation is reversed so that the time dependence F(t) is reconstructed according to $$F(t) = \sum_n A_n \cos(n\omega_1 t + \phi_n).$$

11. A method according to claim 1 in which the rheological material properties are detected as a function of temperature.

12. A method according to claim 1 in which the parameter F is a macroscopically or microscopically acting force variable determined by a macroscopic force measurement or optical measurement of double refraction.

13. Apparatus for detecting rheological material properties of a fluid or flowable material for performing the method according to claim 1 comprising a device for measuring the time function of a characteristic rheological parameter, a device for Fourier transformation of the time function into the Fourier domain and/or reverse transformation, and a control and display unit for setting the operating parameters of the measuring device and for transfer of data from the transformation device.

14. The apparatus according to claim 13 in which the measuring device is a temperature-stabilized oscillating disk or rotational viscosimeter.

15. The apparatus according to claim 13 or 14 further comprising a control loop in which the control and display unit detects the start of a transition of the material to nonlinear response or shear thickening or shear thinning and for issuing a control signal to a drive and/or temperature stabilizing system.

16. Characterizing an operating regime of possible flow mechanisms in states of non-equilibrium selected from a group consisting of extruding, injection molding, stirring, pumping, and laminar casting according to the method of claim 1.

* * * * *